United States Patent [19]
Bock et al.

[11] Patent Number: 5,218,114
[45] Date of Patent: Jun. 8, 1993

[54] CHOLECYSTOKININ ANTAGONISTS

[75] Inventors: Mark G. Bock, Hatfield; Roger M. Freidinger; Robert M. DiPardo, both of Lansdale, all of Pa.

[73] Assignee: Merck & Co., Inc., Rahway, N.J.

[21] Appl. No.: 848,794

[22] Filed: Mar. 10, 1992

Related U.S. Application Data

[63] Continuation-in-part of Ser. No. 763,732, Sep. 23, 1991, abandoned, which is a continuation-in-part of Ser. No. 683,005, Apr. 10, 1991, abandoned.

[51] Int. Cl.$^5$ ............... A61K 31/55; C07D 243/24
[52] U.S. Cl. .................................................. 540/509
[58] Field of Search ....................... 540/309; 514/221

[56] References Cited

U.S. PATENT DOCUMENTS

| 4,820,834 | 4/1991 | Evans et al. | 540/509 |
| 4,994,258 | 2/1991 | Burns et al. | 540/509 |

FOREIGN PATENT DOCUMENTS

| 0304223 | 2/1989 | European Pat. Off. | 514/292 |
| 0349949 | 1/1990 | European Pat. Off. | 540/509 |
| 411668 | 2/1991 | European Pat. Off. | 514/221 |
| 0434364 | 6/1991 | European Pat. Off. | 540/509 |
| 1445874 | 7/1970 | Fed. Rep. of Germany | 514/221 |
| 2150091 | 1/1977 | Fed. Rep. of Germany | 514/221 |
| 92/01683 | 2/1992 | World Int. Prop. O. | 514/221 |

OTHER PUBLICATIONS

Bradwejn, et al., *Enhanced Sensitivity of Cholecystokinin Tetrapeptide in Panic Disorder*, Soc. Neurosci. Abstr. 14(1), p. 291, (1988).
de Montigny, *Cholecystokinin Tetrapeptide Induces Panic Attacks in Healthy Volunteers*, Soc. Neurosci. Abstr. 14(1), p. 291, (1988).
Bradwejn, et al., *Benzodiazepines Antagonize Cholecystokinin—Induced Activation of Rat Hippocampal, Neurones*, Nature 312, p. 22, (1984).
de Montigny, *Cholecystokinin Tetrapeptide Induces Panic-like Attacks in Healthy Volunteers*, Arch. Gen. Psychiatry, 46, pp. 511-517, (1989).
Dourish, et al., *Enhancement of Morphine Analgesia and Prevention of Morphine Tolerance in the Rat by the Cholecystokinin Antagonist L-364,718* Pharm. 147, pp. 469-472, (1988).
Bouthillier, et al., *Long-term Benzodiazepine Treatment Reduces Neuronal Responsiveness to Cholecystokinin: an Electrophysiological Study in the Rat*, Eur. Jour. Pharm. 151, No. 1, pp. 135-138, (1988).
O'Neill et al. *Morphine Induced Analgesia in the Rat Paw Pressure Test is Blocked by CCK and Enhanced by the CCK Antagonist MK-329*, Neuropharmacology 28, No. 3, pp. 243-247 (1989).
Chang, et al., *Biochemical and Pharmacological Characterization of an Extremely Potent and Selective Nonpeptide Cholecystokinin Antagonist*, Proc. Natl. Acad. Sci., 83, pp. 4923-4926 (1986).
Bock, et al., *Benzodiazepine Gastrin and Brain Cholecystokinin Receptor Ligands: L-365,260, Journal of Medicinal Chemistry*, 32, No. 1, pp. 13-16 (1989).
R. M Freidinger, *Cholecystokinin and Gastrin Antagonists*, Medicinal Research Reviews, vol. 9, No. 3, 271-290 (1989).

Primary Examiner—Robert T. Bond
Attorney, Agent, or Firm—Mark R. Daniel; Joseph F. DiPrima

[57] ABSTRACT

Benzodiazepine analogs of the formula:

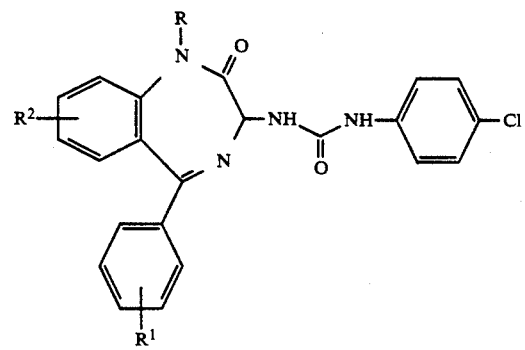

are disclosed which are antagonists of gastrin and cholecystokinin (CCK).

2 Claims, No Drawings

CHOLECYSTOKININ ANTAGONISTS

CROSS REFERENCE

This is a continuation-in-part application of U.S. Ser. No. 07/763,732 filed on Sep. 23, 1991, now abandoned, which is a continuation-in-part application of U.S. Ser. No. 07/683,005 filed on Apr. 10, 1991, now abandoned.

FIELD OF THE INVENTION

This invention relates to the discovery of Benzodiazepine analogs of Formula I for use as antagonists of cholecystokinin (CCK) and gastrin when administered to animals, preferably humans.

BACKGROUND OF THE INVENTION

The Benzodiazepine analogs of Formula I of this invention are useful in treating various diseases caused by an excess of CCK or gastrin. Cholecystokinins (CCK) and gastrin are structurally related neuropeptides which exist in gastrointestinal tissue and in the central nervous system (see, V. Mutt, *Gastrointestinal Hormones*, G. B. J. Glass, Ed., Raven Press, N.Y. p. 169 and G. Nission, ibid, p. 127.

Cholecystokinins include CCK-33, a neuropeptide of thirty-three amino acids and its originally isolated form (see, Mutt and Jorpes, *Biochem. J.* 125, 678 (1971)), its carboxyl terminal octapeptide, CCK-8 (also a naturally-occurring neuropeptide and the minimum fully active sequence), and 39- and 12-amino acid forms. Gastrin occurs in 34-, 17- and 14-amino acid forms, with the minimum active sequence being the C-terminal tetrapeptide, Trp—Met—Asp—Phe—$NH_2$, 2 which is the common structural element shared by both CCK and gastrin.

CCK's are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as also stimulating colonic motility, gall bladder contraction, pancreatic enzyme secretion, and inhibiting gastric emptying. They reportedly co-exist with dopamine in certain mid-brain neurons and thus m ay also play a role in the functioning of dopaminergic systems in the brain, in addition to serving as neurotransmitters in their own right (see: A. J. Prange et al., "Peptides in the Central Nervous System", *Ann. Repts. Med. Chem.* 17, 31, 33 [1982] and references cited therein; J. A. Williams, Biomed. Res. 3 107 [1982]; and J. E. Morley, *Life Sci.* 30, 479, ]1982]).

The primary role of gastrin, on the other hand, appears to be stimulation of the secretion of water and electrolytes in the stomach, and, as such, it is involved in control of gastric acid and pepsin secretion. Other physiological effects of gastrin then include increased mucosal blood flow and increased antral motility. Rat studies have shown that gastrin has a positive trophic effect on the gastric mucosa, as evidenced by increased DNA, RNA and protein synthesis. See e.g. U.S. Ser. No. 452,023.

Antagonists to CCK and to gastrin have been useful for preventing and treating CCK-related and/or gastrin-related disorders of the gastrointestinal (GI) and central nervous (CNS) systems of animals, preferably mammals, and especially those of humans. Just as there is some overlap in the biological activities of CCK and gastrin, antagonists also tend to have affinity for both receptors. In a practical sense, however, there is enough selectivity for the different receptors that greater activity against specific CCK- or gastrin-related disorders can often also be identified.

Selective CCK antagonists are themselves useful in treating CCK-related disorders of the appetite regulatory systems of animals as well as in potentiating and prolonging opiate-mediated analgesia, thus having utility in the treatment of pain [see P. L. Faris et al., *Science* 226, 1215 (1984)]. Selective gastrin antagonists are useful in the modulation of CNS behavior, as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value. See e.g. U.S. Pat. No. 4,820,834. It is further expected that the CCK antagonists of Formula I are useful anxiolytic agents particularly in the treatment of panic and anxiety disorders.

Since CCK and gastrin also have trophic effects on certain tumors [K. Okyama, *Hokkaido J. Med Sci.*, 60, 206–216 (1985)], antagonists of CCK and gastrin are useful in treating these tumors [see R. D. Beauchamp et al., *Ann. Surg.*, 202,303 (1985)].

Distinct chemical classes of CCK-receptor antagonists have been reported R. Freidinger, *Med. Res. Rev.* 9, 271 (1989)]. The first class comprises derivatives of cyclic nucleotides, of which dibutyryl cyclic GMP has been shown to be the most potent by detailed structure-function studies (see, N. Barlas et al., *Am. J. Physiol.*, 242, G 161 (1982) and P. Robberecht et al., *Mol. Pharmacol.*, 17, 268 (1980)).

The second class comprises peptide antagonists which are C-terminal fragments and analogs of CCK, of which both shorter (Boc—Met—Asp—Phe—$NH_2$, Met—Asp—Phe—$NH_2$), and longer (Cbz—Tyr($SO_3H$)—Met—Gly—Trp—Met—Asp—$NH_2$) C-terminal fragments of CCK can function as CCK antagonists, according to recent structure-function studies (see, R. T. Jensen et al., *Biochem. Biophys. Acta.*, 757, 250 (1983), and M. Spanarkel et al., *J. Biol. Chem.*, 258, 6746 (1983)). The latter compound was recently reported to be a partial agonist [see, J. M. Howard et al., *Gastroenterology* 86(5) Part 2, 1118 (1984)].

The third class of CCK-receptor antagonists comprises the amino acid derivatives: proglumide, a derivative of glutaramic acid, and the N-acyl tryptophans including para-chlorobenzoyl-L-tryptophan (benzotript), [see, W. F. Hahne et al., *Proc. Natl. Acad. Sci. U.S.A.*, 78, 6304 (1981), R. T. Jensen et al., *Biochem. Biophys. Acta.*, 761, 269 (1983)]. All of these compounds, however, are relatively weak antagonists of CCK ($IC_{50}$: generally $10^{-4}M$ [although more potent analogs of proglumide have been recently reported in F. Makovec et al., *Arzneim-Forsch Drug Res.*, 35 (II), 1048 (1985) and in German Patent Application DE 3522506A1], but down to $10^{-6}M$ in the case of peptides), and the peptide CCK-antagonists have substantially stability and absorption problems.

In addition, a fourth class consists of improved CCK-antagonists comprising a nonpeptide of novel structure from fermentation sources [R. S. L. Chang et al., *Science*, 230, 177–179 (1985)[ and 3-substituted benzodiazepines based on this structure [published European Patent Applications 167 919, 167 920 and 169 392, B. E. Evans et al, *Proc. Natl. Acad. Sci. U.S.A.*, 83, p.

4918–4922 (1986) and R. S. L. Chang et al, ibid, p. 4923–4926] have also been reported.

No really effective receptor antagonists of the in vivo effects of gastrin have been reported (J. S. Morley, Gut Pept. Ulcer Proc., Hiroshima Symp. 2nd, 1983, p. 1), and very weak in vitro antagonists, such as proglumide and certain peptides have been described [(J. Martinez, J. Med. Chem. 27, 1597 (1984)]. Recently, however, pseudopeptide analogs of tetragastrin have been reported to be more effective gastrin antagonists than previous agents [J. Martinez et al., J. Med. Chem., 28, 1874–1879 (1985)].

A new class of Benzodiazepine antagonist compounds has further been reported which binds selectively to brain CCK (CCK-B) and gastrin receptors [see M. Bock et al., J. Med. Chem., 32, 13–16 (1989)]. One compound of interest reported in this reference to be a potent and selective antagonist of CCK-B receptors is (R)-N-(2,3-dihydro-1-methyl-2-oxo-5-phenyl-1H-1,4-benzodiazepin-3-yl)-N$^1$-(3-methylphenyl) urea (See U.S. Pat. No. 4,820,834.) One disadvantage of the new CCK-B compound reported in Bock et al., J. Med. Chem., 32, 13–16 (1989) and U.S. Pat. No. 4,820,834, is that these CCK-B compounds are poorly water soluble.

It is, therefore, an object of the present invention to provide antagonists of CCK and gastrin. If an antagonist compound could be prepared which would bind with the cell surface receptor of CCK or gastrin, then the antagonist compounds of this invention could be used to block the effect of CCK and gastrin. Another object of the present invention is to provide novel CCK and gastrin antagonist compounds which are water soluble. Other objects of the present invention are to provide methods of inhibiting the action of CCK and gastrin through the administration of novel benzodiazepine analog compounds. The above and other object are accomplished by the present invention in the manner more fully described below.

SUMMARY OF THE INVENTION

The present invention provides Benzodiazepine analogs of the formula:

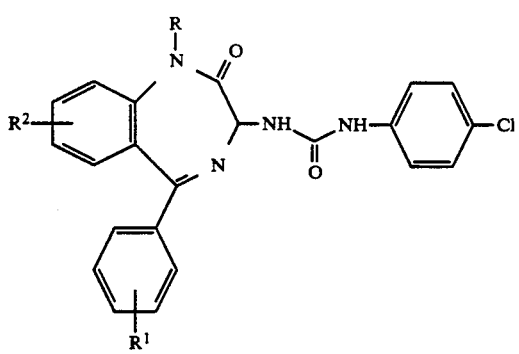

for use as antagonists of CCK and gastrin. The above-mentioned compounds can be used in a method of acting upon a CCK and/or gastrin receptor which comprises administering a therapeutically effective but non-toxic amount of such compound to an animal, preferably a human. A pharmaceutical composition comprising a pharmaceutically acceptable carrier and, dispersed therein, an effective but non-toxic amount of such compound is another aspect of this invention.

DETAILED DESCRIPTION OF THE INVENTION

Benzodiazepine analogs of Formula I provide antagonists of CCK and gastrin. The present invention further provides novel CCK and gastrin antagonist compound which are water soluble. The Benzodiazepine analogs of Formula I are useful in a method of antagonizing the binding of CCK to CCK receptors or antagonizing the binding of gastrin to gastrin receptors. The novel Benzodiazepine analogs of the present invention are illustrated by compounds having the formula:

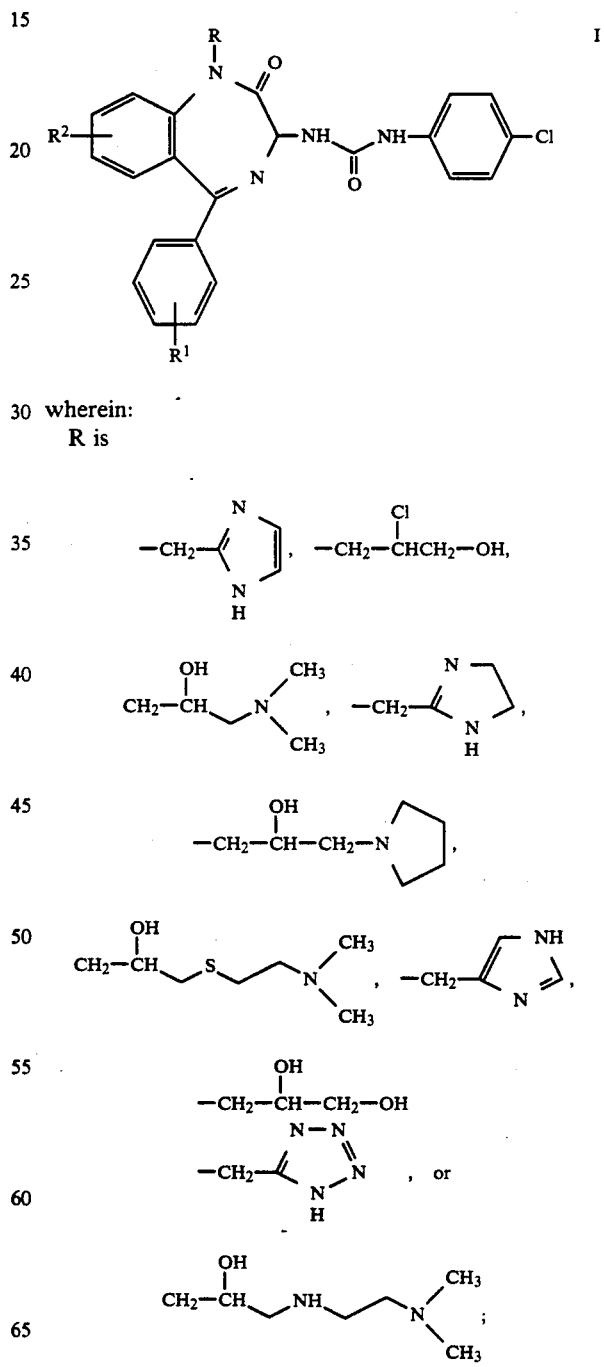

$R^1$ is absent, one or two of Halogen or $CH_3$; and $R^2$ is absent, one or two of Halogen or $CH_3$; or the optical isomers, prodrugs or pharmaceutically acceptable salts thereof.

The preferred compounds of this invention as set forth in the Examples are:

N-{1,3-Dihydro-1-[1H-tetrazol-5-yl]-methyl-2-oxo-5-phenyl-1H-1,4-benzodiazepin-3-yl}-N'-{[4-chlorophenyl]-urea}, N-{1,3-Dihydro-1-[3-((pyrrolidinyl)-2-hydroxy) propyl]-2-oxo-5-phenyl-1H-1,4-benzodiazepin-3-yl}-N'-{[4-chlorophenyl]-urea}, N-{1,3-Dihydro-1-[3-((dimethylamino)-2-hydroxy) propyl]-2-oxo-5-phenyl-1H-1,4-benzodiazepin-3-yl}-N'-{[4-chlorophenyl]-urea}, N-{1,3-Dihydro-1-[3-((hydroxy)-2-chloro)propyl]-2-oxo-5-phenyl-1H-1,4-benzodiazepin-3-yl}-N'-{[4-chlorophenyl]-urea}, or N-{1,3-Dihydro-1-[2,3,-(dihydroxy) propyl]-2-oxo-5-phenyl-1H-1,4-benzodiazepin-3-yl}-N'-{[4-chlorophenyl]-urea}.

It will be appreciated that formula (I) is intended to embrace all possible isomers, including optical isomers, and mixtures thereof, including racemates.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bungaard, Elsevier, 1985.

The pharmaceutically acceptable salts of the compounds of Formula I include the conventional non-toxic salts of the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

The compounds of Formula I antagonize CCK and/or gastrin and are useful as pharmaceutical agents for animals, preferably for mammals, and most especially for humans, for the treatment and prevention of gastrointestinal disorders and central nervous system disorders.

Examples of such gastrointestinal disorders include ulcers, such as peptic and gastrointestinal ulcers, irritable bowel syndrome, gastroesophagenal reflux disease or excess pancreatic or gastrin secretion, acute pancreatitis, or motility disorders, Zollinger-Ellison syndrome, and antral and cell hyperplasia.

Examples of central nervous system disorders include central nervous system disorders caused by CCK interaction with dopamine, such as neuroleptic induced tardive dyskinesia, Parkinson's disease, schizophrenia, other psychosis or Gilles de la Tourette syndrome, and disorders of appetite regulatory systems.

The compounds of Formula I may further be used in the treatment or prevention of additional central nervous system disorders including neurological and psychiatric disorders. Examples of such central nervous system disorders include anxiety disorders and panic disorders, wherein CCK and/or gastrin is involved. Additional examples of central nervous system disorders include panic syndrome, anticipatory anxiety phobic anxiety, panic anxiety, chronic anxiety, and endogenous anxiety.

The compounds of Formula I may further be useful in the treatment of oncologic disorders wherein CCK or gastrin may be involved. Examples of such oncologic disorders include small cell adenocarcinomas and primary tumors of the central nervous system glial and neuronal cells. Examples of such adenocarcinomas and tumors include, but are not limited to, tumors of the lower esophagus, stomach, intestine, colon and lung, including small cell lung carcinoma.

The compounds of Formula I may further be used to control pupil constriction in the eye. The compounds may be used for therapeutic purposes during eye examinations and intraocular surgery in order to prevent miosis. The compounds may further be used to inhibit miosis occurring in association with iritis, uveitis and trauma.

The compounds of Formula I are also useful for directly inducing analgesia, opiate or non-opiate mediated, as well as anesthesia or loss of the sensation of pain.

The compounds of Formula I may further be useful for preventing or treating the withdrawal response produced by chronic treatment or abuse of drugs or alcohol. Such drugs include, but are not limited to cocaine, alcohol or nicotine.

The present invention also encompasses a pharmaceutical composition useful in the treatment of CCK and/or gastrin disorders comprising the administration of a therapeutically effective but non-toxic amount of the compounds of Formula I, with or without pharmaceutically acceptable carriers or diluents.

The compounds of formula (I) may also be useful as neuroprotective agents, for example, in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by neurotoxins, including environmental neurotoxins.

The compounds of Formula I, may be administered to animals, preferably to mammals, and most especially to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to Formula I is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.005 mg/kg to about 50 mg/kg of body weight, and preferably, of from about 0.05 mg/kg to about 50 mg/kg of body weight, and most preferably, of from about 0.5 mg/kg to about 20 mg/kg of body weight, administered in single or divided doses.

In some cases, however, it may be necessary to use dosage levels outside these limits. For example, doses as low as about 1 ng/kg, about 0.005 µg to about 0.05 µg, or about 100 ng to about 100 µg/kg may be administered.

In the effective treatment of panic syndrome, panic disorder, anxiety disorder and the like, preferably about 0.05 mg/kg to about 1.0 mg/kg of CCK antagonist maybe administered orally (p.o.), administered in single or divided doses per day (b.i.d.). Other routes of administration are also suitable.

For directly inducing analgesia, anesthesia or loss of pain sensation, the effective dosage range is preferably from about 100 ng/kg to about 1 mg/kg by intraperitoneal administration. Oral administration is an alternative route, as well as others.

In the treatment of irritable bowel syndrome, preferably about 0.1 to 10 mg/kg of CCK antagonist is administered orally (p.o.), administered in single or divided doses per day (b.i.d.). Other routes of administration are also suitable.

The use of a gastrin antagonist as a tumor palliative for gastrointestinal neoplasma with gastrin receptors, as a modulator of central nervous activity, treatment of Zollinger - Ellison snydrome, or in the treatment of peptic ulcer disease, an effective dosage is preferably from 0.1 to about 10 mg/kg administered one-to-four times daily is indicated.

Because these compounds antagonize the function of CCK in animals, they may also be used as feed additives to increase the food intake of animals in daily dosage preferably from about 0.05 mg/kg to about 50 mg/kg of body weight.

The compounds of Formula I may be prepared according to the reaction schemes as set forth below.

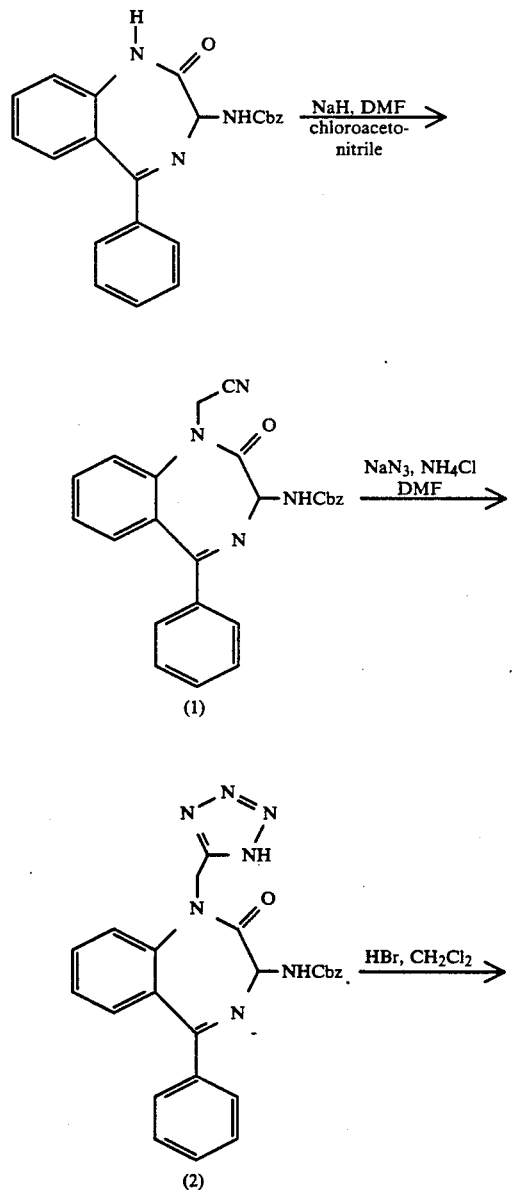

-continued
SCHEME 1
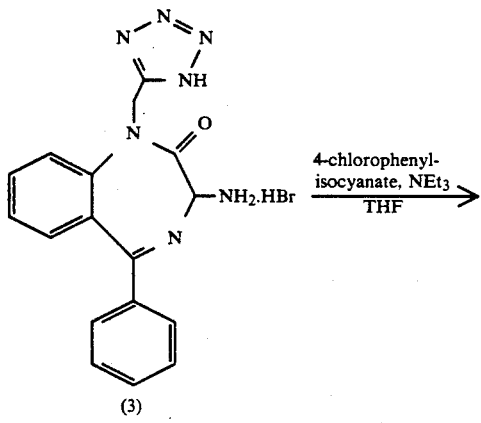
(3)
4-chlorophenyl-
isocyanate, NEt3
———————→
THF
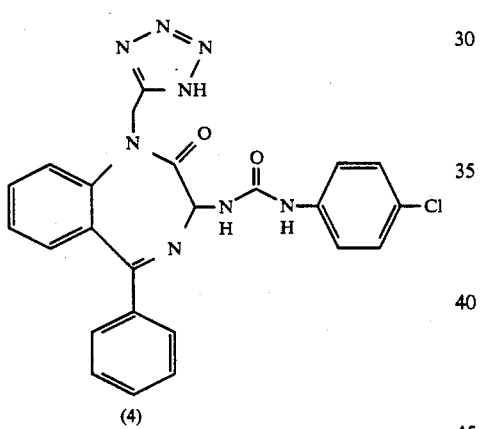
(4)
SCHEME 2
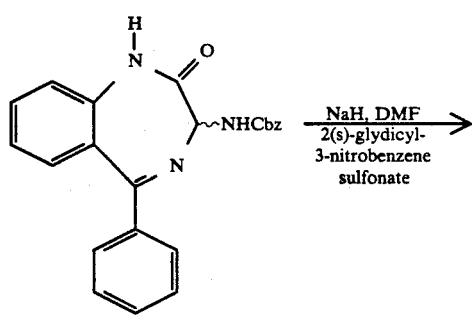
NaH, DMF
——————————→
2(s)-glydicyl-
3-nitrobenzene
sulfonate
-continued
SCHEME 2
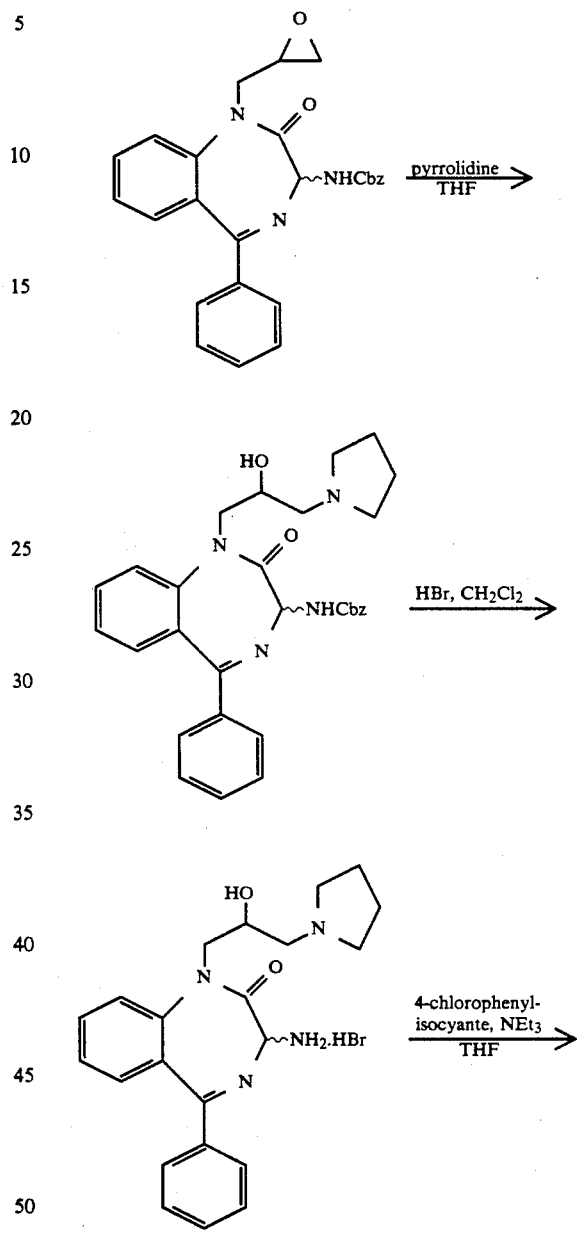
pyrrolidine
—————→
THF
HBr, CH2Cl2
——————→
4-chlorophenyl-
isocyante, NEt3
———————→
THF
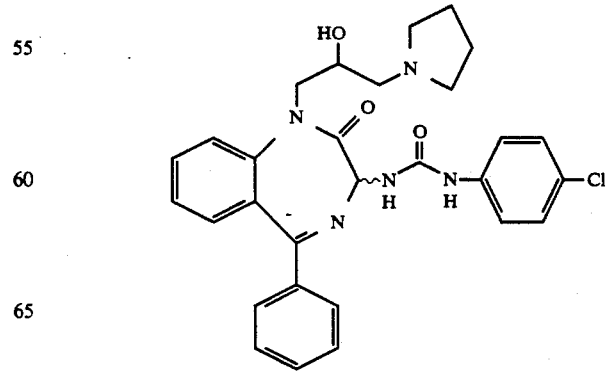

SCHEME 3

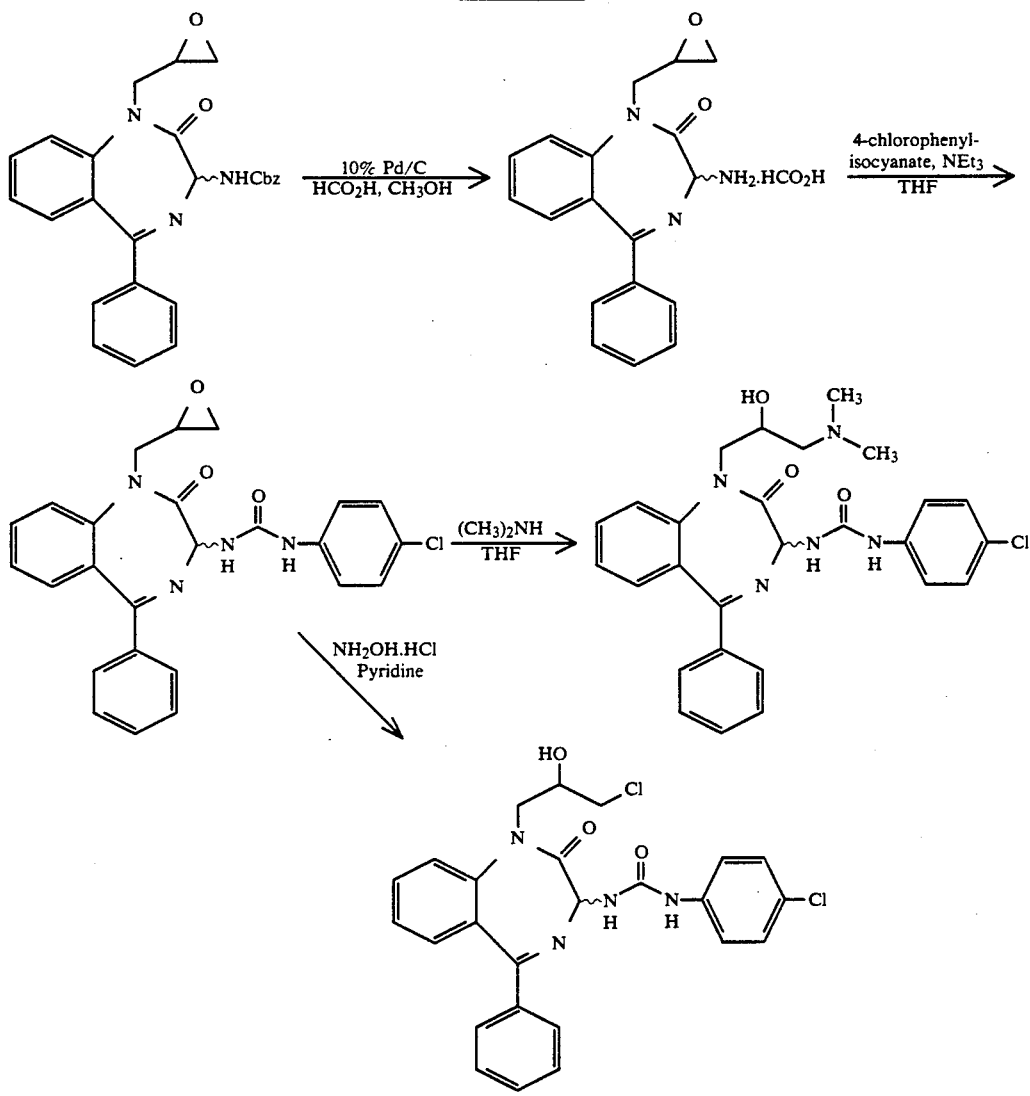

1. CCK Receptor Binding (Pancreas)

CCK-8 sulphated was radiolabelled with $^{125}$I-Bolton Hunter reagent (2000 Ci/mmole). Receptor binding was performed according to Chang and Lotti (Proc. Natl. Acad. Sci. 83, 4923–4926, 1986) with minor modifications.

Male Sprague-Dawley rats (150–200 g) were sacrificed by decapitation. The whole pancreas was dissected free of fat tissue and was homogenized in 25 volumes of ice-cold 10 mM Hepes buffer with 0.1% soya bean trypsin inhibitor (pH 7.4 at 25° C.) with a Kinematica Polytron. The homogenates were centrifuged at 47,800 g for 10 min. Pellets were resuspended in 10 volumes of binding assay buffer (20 mM Hepes, 1 mM EGTA, 5 mM MgCl$_2$, 150 mM NaCl, bacitracin 0.25 mg/ml, soya bean trypsin inhibitor 0.1 mg/ml, and bovine serum albumin 2 mg/ml, pH 6.5 at 25° C.) using a teflon homogenizer, 15 strokes at 500 rpm. The homogenate was further diluted in binding assay buffer to give a final concentration of 0.5 mg original wet weight/1 ml buffer. For the binding assay, 50 μl of buffer (for total binding) or unlabeled CCK-8 sulfated to give a final concentration of 1 μM (for nonspecific binding) or the compounds of Formula I (for determination of inhibition of $^{125}$I-CCK binding) and 50 μl of 500 pM $^{125}$I-CCK-8 (i.e. 50 pM final concentration) were added to 400 μl of the membrane suspensions in microfuge tubes. All assays were run in duplicate. The reaction mixtures were incubated at 25° C. for 2 hours and the reaction terminated by rapid filtration (Brandell 24 well cell harvester) over Whatman GF/C filters, washing 3×4 mls with ice-cold 100 mM NaCl. The radioactivity on the filters was counted with a LKB gamma counter.

2. CCK Receptor Binding (Brain)

CCK-8 sulphated was radiolabelled and the binding was performed according to the description for the pancreas method with minor modifications.

Male Hartley guinea pigs (300–500 g) were sacrificed by decapitation and the cortex was removed and homogenized in 25 mL ice-cold 0.32M sucrose. The homogenates were centrifuged at 1000 g for 10 minutes and the resulting supernatant was recentrifuged at 20,000 g for 20 minutes. The P$_2$ pellet was resuspended in binding assay buffer (20 mM N-2-hydroxyethyl-piperazine-N'-2-ethane sulfonic acid (HEPES), 5 mM MgCl$_2$, 0.25 mg/ml bacitracin, 1 mM ethylene glycol-bis-(β-aminoethylether-N,N'-tetraacetic acid) (EGTA)pH 6.5 at 25° C., using a teflon homogenizer (5 strokes at 500 rpm) to give a final concentration of 10 mg original wet weight 11.2 mls buffer. For the binding assay, 50 μl of buffer (for total binding) or unlabeled CCK-8 sulfate to give a final concentration of 1 μM (for nonspecific binding) or the compounds of Formula I (for determination of inhibition of $^{125}$I-CCK-8 binding) and 50 μl of 500 pM $^{125}$I-CCK-8 (i.e. final concentration of 50 pM) were added to 400 μl of the membrane suspensions in microfuge tubes. All assays were run in duplicate. The reaction mixtures were incubated at 25° C. for 2 hours and then the reaction was terminated on Whatman GF/C filters by rapid filtration (Brandell 24 well cell Harvester) with 3×5 ml washes of cold 100 mM NaCl. The radioactivity on the filters was then counted with a LKB gamma counter.

3. Gastrin Antagonism

Gastrin antagonist activity of compounds of Formula I is determined using the following assay.

A. GASTRIN RECEPTOR BINDING IN GUINEA PIG GASTRIC GLANDS

Preparation of guinea pig gastric mucosal glands

Guinea pig gastric mucosal glands were prepared by the procedure of Chang et al., Science 230, 177–179 (1985) with slight modification. Gastric mucosa from guinea pigs (300–500 g body weight, male Hartley) were isolated by scraping with a glass slide after washing stomachs in ice-cold, aerated buffer consisting of the following: 130 mM NaCl, 12 mM NaHCO$_3$, 3 mM NaH$_2$PO$_4$, 3 mM Na$_2$HPO$_4$, 3 mM K$_2$HPO$_4$, 2 mM MgSO$_4$, 1 mM CaCl$_2$, 5 mM glucose and 4 mM L-glutamine, 50 mM HEPES, 0.25 mg/ml bacitracin, 0.10 mg/ml soya bean trypsin inhibitor, 0.1 mg/ml bovine serum albumin, at pH 6.5, and then incubated in a 37° C. shaking water bath for 40 minutes in buffer containing 1 mg/ml collagenase and bubbled with 95% O$_2$ and 5% CO$_2$. The tissues were passed twice through a 5 ml syringe to liberate the gastric glands, and then filtered through Nitex #202 gauge nylon mesh. The filtered glands were centrifuged at 272 g for 5 minutes and washed twice by resuspension in 25 ml buffer and centrifugation.

B. BINDING STUDIES

The washed guinea pig gastric glands prepared as above were resuspended in 25 ml of standard buffer. For binding studies, to 250 μl of gastric glands, 30 μl of buffer (for total binding) or gastrin (3 μM final concentration, for nonspecific binding) or test compound and 20 μl of $^{125}$I-gastrin (NEN, 2200 Ci/mmole, 0.1 nM final concentration) were added. AV assays were run in triplicate. The tubes were aerated with 95% O$_2$ and 5% CO$_2$ and capped. The reaction mixtures after incubation at 25° C. for 30 minutes in a shaking water bath were rapidly filtered (Brandell 24 well cell harvester) over Whatman and G/F B filters presoaked in assay buffer and immediately washed further with 3×4 ml of 100 mM ice cold NaCl. The radioactivity on the filters was measured using a LKB gamma counter.

IN VITRO RESULTS

Effect of The Compounds of Formula I on $^{125}$I-CCK-8 receptor binding

The preferred compounds of Formula I are those which produced dose-dependent inhibition of specific $^{125}$I-CCK-8 binding as defined as the difference between total and non-specific (i.e. in the presence of 1 μm CCK) binding.

Drug displacement studies were performed with at least 10 concentrations of compounds of formula 1 and the IC$_{50}$ values were determined by regression analysis. IC$_{50}$ refers to the concentration of the compound required to inhibit 50% of specific binding of $^{125}$I-CCK-8.

The data in Table I were obtained for compounds of Formula I.

TABLE I

| CCK RECEPTOR BINDING RESULTS IC$_{50}$ (μM) | | | |
|---|---|---|---|
| Compound of Ex # | $^{125}$I-CCK Pancreas | $^{25}$I-CCK Brain | $^{25}$I-Gastrin Gastric Glands |
| 1 | 2.13 | 0.494 | N.D. |
| 2 | >3 | 0.3 | N.D. |
| 3 | >3 | 0.43 | N.D. |
| 4 | >3 | 0.062 | N.D. |
| 5 | >3 | 0.118 | N.D. |

N.D. = NO DATA

EXAMPLES

Examples provided are intended to assist in a further understanding of the invention. Particular materials employed, species and conditions are intended to be further illustrative of the invention and not limitative of the reasonable scope thereof.

EXAMPLE 1

Synthesis of
N-{1,3-Dihydro-1-[1H-tetrazol-5yl]methyl-2-oxo-5-phenyl-1H-1,4-benzodiazepin-3-yl}-N'-{[4-chlorophenyl]-urea}

A)
1,3-Dihydro-1-cyanomethyl-3-[(benzyloxycarbonyl)amino]-5-phenyl-2H-1,4-benzodiazepin-2-one. (1)

1,3-Dihydro-3(R,S)-[(benzyloxycarbonyl)amino]-5-phenyl-2H-1,4-benzodiazepin-2-one (1.5 g) was dissolved in 25 ml of dry N,N-dimethylformamide at 0° C. To this solution was added 218 mg of (60%) sodium hydride and the resulting reaction mixture was stirred for 15 minutes. Chloroacetonitrile in 1 ml of dry N,N-dimethylformamide was then added and the reaction mixture was allowed to warm to room temperature. After 1 hour the reaction mixture was concentrated under reduced pressure and the residue was partitioned between ethyl acetate and 10% citric acid solution. The organic phase was washed with brine, then dried (sodium sulfate), and concentrated to give a solid. The title compound (1.53 g, 93%) was obtained in pure form after flash silica gel chromatography employing ethyl acetate-hexane (1:2 v/v) as eluant.

B)
1,3-Dihydro-1-(1H-tetrazol-5-yl)methyl-3-[(benzyloxycarbonyl)amino]-5-phenyl-2H-1,4-benzodiazepin-2-one. (2)

A mixture of 150 mg of 1,3-dihydro-1-cyanomethyl-3-[(benzyloxycarbonyl)amino]-5-phenyl-2H-1,4-benzodiazepin-2-one, 124 mg of sodium azide, and 102 mg of ammonium chloride was heated in 3 ml of dry N,N-dimethylformamide at 110° C. for 4 hours. The reaction mixture was concentrated in vacuo and the residue was suspended in water, acidified with 1N HCl solution, and extracted twice with ethyl acetate. The combined organic extracts were dried (sodium sulfate) and concentrated to give 180 mg of crude product. Purification via preparative thick layer chromatography on 4 1.0 mm×20 cm×20 cm silica gel plates (90:10:1, chloroform-methanol-acetic acid elution) afforded 99 mg of the title compound.

C)
1,3-Dihydro-1-(1H-tetrazol-5-yl)methyl-3-amino-5-phenyl-2H-1,4-benzodiazepin-2-one hydrobromide (3)

1,3-Dihydro-1-(1H-tetrazol-5-yl)methyl-3-(benzyloxycarbonyl)amino]-5-phenyl-2H-1,4-benzodiazepin-2-one (95 mg) was dissolved in 10 ml of methylene chloride. The resulting solution was cooled to 0° C. and saturated with hydrogen bromide gas for 10 minutes. The reaction vessel was sealed and the reaction mixture was allowed to warm to room temperature over 0.5 hours. The vessel was vented and the solvent and excess hydrogen bromide gas were removed under reduced pressure to give 110 mg of the title compound.

D)
N-{1,3-Dihydro-1-(1H-tetrazol-5-yl)methyl-2-oxo-5-phenyl-1H-1,4-benzodiazepin-3-yl}-N'-{N-chlorophenyl]urea}. (4)

1,3-Dihydro-1-(1H-tetrazol-5-yl)methyl-3-amino-5-phenyl-2H-1,4,benzodiazepin-2-one hydrobromide (55 mg) was suspended in 2 ml of dry tetrahydrofuran. To this suspension was added in succession 14.6 μL of triethylamine and 16.1 mg of 4-chlorophenylisocyanate. Enough triethylamine was added to maintain the pH at 8 (36.5 μL total). The reaction mixture was protected from moisture and was allowed to stir at room temperature for 2 hours. The reaction mixture was filtered and the filtrate was concentrated to 1 ml under reduced pressure. The residual material was chromatographed on three 0.5 mm×20 cm×20 cm precoated silica gel plates (chloroform-methanol-acetic acid elution, 90:10:1 v/v). In this way, 10 mg of the title compound was obtained in analytical form: m.p. >190° C. (d).

HPLC=97.7% pure at 214 nm; TLC $R_f$=0.15 ($CHCl_3$—$CH_3OH$—HOAc, 90:10:1, v/v).

NMR (DMSO-$D_6$): Consistent with structure assignment and confirms presence of solvent.

FAB MS: 487 (M+ +1).

Analysis for $C_{24}H_{19}Cl_1N_8O_2$·2.25 HOAc·0.75 $H_2O$: Calculated: C, 53.86; H, 4.68; N, 17.63 Found: C, 53.85; H, 4.34; N, 17.64.

EXAMPLE 2

Synthesis of
N-{1,3-Dihydro-1-[3-((pyrrolidinyl)-2-hydroxy)propyl]-2-oxo-5-phenyl-1H-1,4-benzodiazepin-3-yl}-N'-{[4-chlorophenyl]-urea}

1,3-Dihydro-1-(2-oxiranyl)methyl-5-phenyl-3-[(benzyloxycarbonyl)amino]-2H-1,4-benzodiazepin-2-one 1,3-Dihydro-5-phenyl-3(R,S)-[(benzyloxycarbonyl)amino]-2H-1,4-benzodiazepin-2-one (1.52 g) was dissolved in 10 ml of dry N,N-dimethylformamide at 0° C. To this solution was added 190 mg of (60%) sodium hydride and the resulting reaction mixture was stirred for 60 minutes. 2-S-(+)-Glycidyl-3-nitrobenzenesulfonate (1.23 g) in 1 ml of dry N,N-dimethylformamide was then added and the reaction mixture was allowed to warm to room temperature. After 12 hours the reaction mixture was quenched by the careful addition of water and was then concentrated under reduced pressure. The residue was dissolved in ethyl acetate and this solution was washed with water and brine. Concentration of the dried ($Na_2SO_4$) organic extracts afforded a semi-solid which was flash chromatographed on silica gel (hexane-ethyl acetate, 4:1 v/v) to give the title compound (1.7 g) as a white solid.

1,3-Dihydro-1-[3-((pyrrolidinyl)-2-hydroxy)propyl]-5-phenyl-3-[(benzyloxycarbonyl)amino]-2H-1,4-benzodiazepin-2-one 1,3-Dihydro-1-(2-oxiranyl)methyl-5-phenyl-3-[(benzyloxycarbonyl)amino]-2H-1,4-benzodiazepin-2-one (150 mg, 0.34 mmol) and 34 μL pyrrolidine were combined in 2 ml of tetrahydrofuran. The resulting solution was heated to 55° C. After 8 and 12 hours reaction time, more pyrrolidine (34 μL and 30 μL, respectively) as added. The reaction was complete after 21 hours at 55° C. The solvent and excess pyrrolidine were removed under reduced pressure and the residue was chromatographed utilizing three 1 mm precoated silica gel plates (chloroform-methanol-concentrated ammonium hydroxide 92:8:0.8, development). The title compound (124 mg) was obtained as a mixture of diastereomers and was used directly in the next reaction.

1,3-Dihydro-1-[3-((pyrrolidinyl)-2-hydroxy)propyl]-5-phenyl-3-amino-2H-1,4-benzodiazepin-2-one formate salt The above mixture of diastereometric 1,3-dihydro-1-[3-((pyrrolidinyl)-2-hydroxy)propyl]-5-phenyl-3-[(benzyloxycarbonyl)amino]-2H-1,4-benzodiazepin-2-ones (124 mg) was dissolved in 40 ml of solvent mixture containing 4.5% formic acid (90%) in methanol. The reaction flask was flushed with nitrogen and 40 mg of 10% palladium/carbon catalyst was added. The resulting suspension was stirred vigorously under nitrogen at room temperature for 2.5 hours. The reaction mixture was filtered through Celite and the filtrated was concentrated under reduced pressure. The resulting residue was azeotropically dried with toluene to give 139 mg of the title compound as the formate salt.

N-{1,3-Dihydro-1-[3-((pyrrolidinyl)-2-hydroxy)propyl]-2-oxo-5-phenyl-1H-1,4-benzodiazepin-3-yl}-N'-{[4-chlorophenyl]-urea}

To a solution of 139 mg (0.327 mmole) of 1,3-dihydro-1-[3-((pyrrolidinyl)-2-hydroxy)propyl]-5-phenyl-3-amino-2H-1,4-benzodiazepin-2-one formate salt in a 4 ml of dry tetrahydrofuran containing 41 μL of triethylamine was added 45 mg (0.295 mmole) of 4-chlorophenylisocyanate at 0° C. The reaction mixture was stirred for 30 minutes and then concentrated to 1 ml. This solution was applied to six 0.5 mm precoated silica gel plates (chloroform-methanol development, 9:1 v/v) to give the title compound in analytically pure form as a mixture of diastereomers after trituration with ethyl ether-methanol: m.p. >206° C. (d).

HPLC=99.8% pure at 214 nm;

NMR(DMSO-$D_6$): Consistent with structure assignment and confirms presence of solvent.

FAB MS: 532 (M+ +1).

Analysis for $C_{29}H_{30}ClN_5O_3 \cdot 1.00\ H_2O$: Calculated: C, 63.32; H, 5.86; N, 12.73. Found: C, 63.32; H, 5.49; N, 12.38.

EXAMPLE 3

Synthesis of
N-{1,3-Dihydro-1-[3-((dimethylamino)-2-hydroxy)-propyl]-2-oxo-5-phenyl-1H-1,4-benzodiazepin-3-yl}-N'-{[4-chlorophenyl]-urea}

1,3-Dihydro-1-(2-oxiranyl)methyl-5-phenyl-3-amino-2H-1,4-benzodiazepin-2-one formate salt A mixture of 1,3-dihydro-1-(2-oxiranyl)methyl-5-phenyl-3-[(benzyloxycarbonyl)amino]-2H-1,4-benzodiazepin-2-ones (530 mg) was dissolved in 70 ml of solvent mixture containing 4.5% formic acid (90%) in methanol. The reaction flask was flushed with nitrogen and 170 mg of 10% palladium/carbon catalyst was added. The resulting suspension was stirred vigorously under nitrogen at room temperature for 1 hour. The reaction mixture was filtered through Celite and the filtrated was concentrated under reduced pressure. The resulting residue was azeotropically dried with toluene to give 402 mg of the title compound as the formate salt.

N-{1,3-Dihydro-1-(2-oxiranyl)methyl-2-oxo-5-phenyl-1H-1,4-benzodiazepin-3-yl}-N'-{[4-chlorophenyl]-urea}

1,3-Dihydro-1-(2-oxiranyl)methyl-5-phenyl-3-amino-2H-1,4-benzodiazepin-2-one formate salt (427 mg, 1.21 mmole) was dissolved in 3 ml of tetrahydrofuran. The resulting solution was rendered alkalanine with trietylamine (pH 8). The reaction mixture was then cooled to 0° C. and treated with 186 mg (1.21 mmole) of 4-chlorophenylisocyanate in one portion. The reaction mixture was allowed to stand at 0° C. for 15 minutes and the was applied directly to six 1 mm precoated silica gel plates. Development with chloroform-methanol-concentrated ammonium hydroxide (94:6:0.6, v/v) gave the title compound as a white solid (400 mg). N-{1,3-Dihydro-1-[3-((dimethylamino)-2-hydroxy)propyl]-2-oxo-5-phenyl-1H-1,4-benzodiazepin-3-yl}-N'{[4-chlorophenyl]-urea}

A solution of 6 ml of tetrahydrofuran containing 56 mg of N-{1,3-dihydro-1-(2-oxiranyl)methyl-2-oxo-5-phenyl-1H-1,4-benzodiazepin-3-yl}-N'-{[4-chlorophenyl]-urea} was cooled to 0° C. and saturated with dimethylamine. The reaction vessel was capped with a rubber septum and the reaction mixture was allowed to stand at room temperature for 60 hours. The solvent was removed in vacuo and the residue was chromatographed via preparative thick layer plates (0.5 mm thickness, chloroform-methanol-concentrated ammonium hydroxide (98:2:0.2, development) to give 32 mg of the title compound as a mixture of diastereomers: m.p. 219°–221° C. (d).

HPLC=96.5% pure at 214 nm;

NMR(DMSO-$D_6$): Consistent with structure assignment and confirms presence of solvent.

FAB MS: 506 (M+ +1).

Analysis for $C_{27}H_{28}ClN_5O_3 \cdot 0.15 CHCl_3$: Calculated: C, 62.24; H, 5.42; N, 13.37. Found: C, 63.10; H, 5.28; N, 13.37.

EXAMPLE 4

Synthesis of
N-{1,3-Dihydro-1-[3-((hydroxy)-2-chloro)propyl]-2-oxo-5-phenyl-1H-1,4-benzodiazepin-3-yl}-N'-{[4-chlorophenyl]-urea}

A solution of N-{1,3-dihydro-1-(2-oxiranyl)methyl-2-oxo-5-phenyl-1H-1,4-benzodiazepin-3-yl}-N'-}[4-chlorophenyl]-urea} (135 mg, 0.293 mmole) in 5 ml of pyridine was treated with 60 mg of hydroxylamine hydrochloride. The reaction mixture was stirred for 60 hours at room temperature and concentrated under reduced pressure. The residue was azeotropically dried with toluene and was then purified by preparative thick layer chromatography on silica gel (chloroform-methanol-concentrated ammonium hydroxide development, 90:10:1) to give an off-white solid. Recrystallization from methanol afforded 40 mg of the title compound in analytically pure form: m.p. 225° C. (d).

HPLC=>93% pure at 214 nm;

NMR(DMSO-$D_6$): Consistent with structure assignment and confirms presence of solvent.

FAB MS: 497 (M+ +1).

Analysis for $C_{25}H_{22}ClN_4O_3 \cdot 0.15 CHCl_3 \cdot 0.15 CH_3OH$: Calculated: C, 58.42; H, 4.41; N, 10.77. Found: C, 58.40; H, 4.03; N, 10.98.

EXAMPLE 5

Synthesis of
N-{1,3-Dihydro-1-[2,3-(dihydroxy)propyl]-2-oxo-5-phenyl-1H-1,4-benzodiazepin-3-yl}-N'-{[4-chlorophenyl]-urea}

To a solution of N-{1,3-dihydro-1-(2-oxiranyl)methyl-2-oxo-5-phenyl-1H-1,4-benzodiazepin-3-yl}-N'-{[4-chlorophenyl]-urea} (58 mg, 0.126 mmole) in 1.5 ml of glacial acetic acid was added 100 $\mu L$ of water. After 18 hours at room temperature the solvent was removed under reduced pressure and the residue was chromatographed via preparative thick layer chromatography (chloroform-methanol-concentrated ammonium hydroxide development, 92:8:0.8). The analytical sample (39 mg) was obtained as a white solid: m.p. 232°–234° C. (d).

HPLC=>99% pure at 214 nm;

NMR(DMSO-$D_6$): Consistent with structure assignment and confirms presence of solvent.

FAB MS: 479 (M+ +1).

Analysis for $C_{25}H_{23}ClN_4O_4 \cdot 0.05 CHCl_3$: Calculated: C, 62.04; H, 4.79; N, 11.56. Found: C, 62.06; H, 4.74; N, 11.39.

What is claimed is:

1. A compound of Formula I:

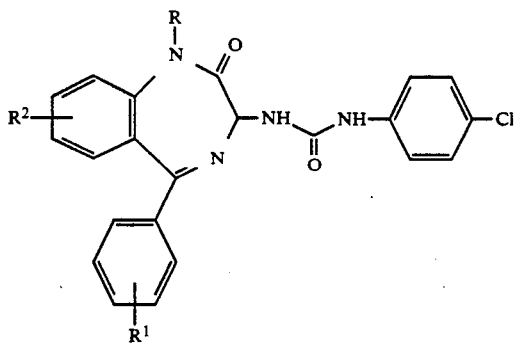

wherein:

R is

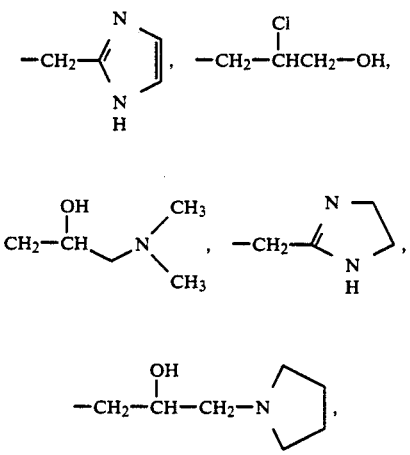

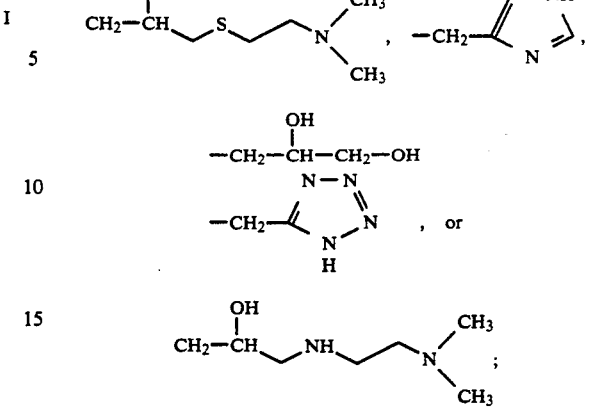

R¹ is absent, one or two of Halogen or CH₃; and
R² is absent, one or two of Halogen or CH₃; or the optical isomers, prodrugs or pharmaceutically acceptable salt thereof.

2. The compound of claim 1, in which the compound is N-{1,3-Dihydro-1-[1H-tetrazol-5-yl]-methyl-2-oxo-5-phenyl-1H-1,4-benzodiazepin-3-yl}-N'-{[4-chlorophenyl]-urea}, N-{1,3-Dihydro-1-[3-((pyrrolidinyl)-2-hydroxy) propyl]-2-oxo-5-phenyl-1H-1,4-benzodiazepin-3-yl}-N'-{[4-chlorophenyl]-urea}, N-{1,3-Dihydro-1-[3-((dimethylamino)-2-hydroxy) propyl]-2-oxo-5-phenyl-1H-1,4-benzodiazepin-3-yl}-N'-[4-chlorophenyl]-urea}, N-{1,3-Dihydro-1-[3-((hydroxy)-2-chloro)propyl]-2-oxo-5-phenyl-1H-1,4-benzodiazepin-3-yl}-N'-{[4-chlorophenyl]-urea}, or N-{1,3-Dihydro-1-[2,3,-(dihydroxy) propyl]-2-oxo-5-phenyl-1H-1,4-benzodiazepin-3-yl}-N'-{[4-chlorophenyl]-urea} or a pharmaceutically acceptable salt thereof.

* * * * *